(12) United States Patent
Martin

(10) Patent No.: US 9,968,143 B2
(45) Date of Patent: May 15, 2018

(54) SLEEVE WITH LINING LAYER FOR BODY PART PROTECTION OR CARE

(75) Inventor: Jean-Luc Martin, Loriol sur Drome (FR)

(73) Assignee: Millet Innovation, Loriol sur Drôme (FR)

( * ) Notice: Subject to any disclaimer, the term of this patent is extended or adjusted under 35 U.S.C. 154(b) by 1474 days.

(21) Appl. No.: 12/105,308

(22) Filed: Apr. 18, 2008

(65) Prior Publication Data

US 2008/0262403 A1 Oct. 23, 2008

Related U.S. Application Data

(63) Continuation of application No. PCT/FR2006/002231, filed on Oct. 4, 2006.

(30) Foreign Application Priority Data

Oct. 20, 2005 (FR) ..................................... 05 10670

(51) Int. Cl.
*A61F 13/06* (2006.01)
*A41D 13/08* (2006.01)
*A61F 5/01* (2006.01)
*A61F 13/10* (2006.01)
*A61F 13/00* (2006.01)

(52) U.S. Cl.
CPC .......... *A41D 13/087* (2013.01); *A61F 5/0109* (2013.01); *A61F 13/068* (2013.01); *A61F 13/105* (2013.01); *A61F 2013/00093* (2013.01)

(58) Field of Classification Search
CPC ...... A41D 13/087; A41D 13/08; A41D 13/05; A41D 13/0543; A41D 13/06; A61F 5/0109; A61F 13/068; A61F 13/105; A61F 2013/00093; A61F 5/01; A61F 5/0104; A61F 5/0106; A61F 5/0118; A61F 5/019; A61F 13/04; A61F 13/06; A61F 13/061; A61F 13/064; A61F 13/065; A61F 13/067; A61F 13/08; A61F 13/10; A61F 13/104; B32B 37/0076; B32B 37/065; B32B 37/30; Y10T 156/1036; B29C 65/08; B29C 66/4322; B29C 66/432; B29C 66/4332; B29C 66/4312
USPC ...... 602/63, 62, 23; 156/217, 218, 267, 148, 156/73.1, 308.4
See application file for complete search history.

(56) References Cited

U.S. PATENT DOCUMENTS

| | | | |
|---|---|---|---|
| 2,044,523 A | | 6/1936 | Bertram |
| 2,506,916 A | * | 5/1950 | Bishop .................. B29C 53/387 156/218 |
| 3,648,291 A | | 3/1972 | Pankers |

(Continued)

FOREIGN PATENT DOCUMENTS

| | | |
|---|---|---|
| FR | 2 712 487 A1 | 5/1995 |
| WO | 00/71066 A1 | 11/2000 |

*Primary Examiner* — Victoria J Hicks
(74) *Attorney, Agent, or Firm* — Panitch Schwarze Belisario & Nadel LLP

(57) ABSTRACT

A protective sleeve is provided for the care of fingers, toes or other parts of the body. The sleeve is made of a piece of fabric, preferably including thermoplastic fibers. The piece of fabric includes opposite edges which are assembled to form the body of the sleeve. At least one lining layer, preferably of viscoelastic gel, is fixed onto a face of the piece of fabric, such that the layer at least partially covers the assembled edges of the piece of fabric.

11 Claims, 2 Drawing Sheets

(56) References Cited

U.S. PATENT DOCUMENTS

| | | | | |
|---|---|---|---|---|
| 4,446,181 | A | * | 5/1984 | Wood ............... B29C 53/36 |
| | | | | 112/424 |
| 5,382,223 | A | * | 1/1995 | Springs ............... A61F 5/01 |
| | | | | 156/217 |
| 5,383,846 | A | | 1/1995 | Short |
| 2002/0095107 | A1 | * | 7/2002 | Martin ............... A61F 13/06 |
| | | | | 602/61 |

* cited by examiner

SLEEVE WITH LINING LAYER FOR BODY PART PROTECTION OR CARE

CROSS-REFERENCE TO RELATED APPLICATIONS

This application is a Continuation of International Application No. PCT/FR2006/002231, filed Oct. 4, 2006, which was published in the French language on Apr. 26, 2007, under International Publication No. WO 2007/045737 A2 and the disclosure of which is incorporated herein by reference.

BACKGROUND OF THE INVENTION

The present invention relates to the field of dressings in the form of a sleeve for the protection and care of fingers, toes and, more generally, limbs of the human body. The ends of the limbs of the human body are exposed to a lot of stress, causing injuries or conditions that require means of protection or care.

For this purpose, there are various structures and shapes of sleeves comprising viscoelastic materials. Tubular sleeves consisting solely of viscoelastic polymers are known in particular. The disadvantage of these sleeves is that the polymer tube must combine mechanical properties of elasticity, resistance, viscoelasticity, and little encumbrance, which are contradictory and are not combined in a satisfactory manner to the detriment of the physiological effects of the sleeve. Woven sleeves comprising a lining of viscoelastic material are also known. These sleeves have the disadvantage of being cumbersome, as the fabric and the lining must have a significant thickness due to the poor mechanical properties of the materials used. In addition, to solve the problem of industrially producing a tubular sleeve made of fabric, loose-knit fabrics are used to the detriment of the thickness and hold of the sleeve and of user comfort.

European Patent EP 1 191 912 B describes a protective sleeve for the care of fingers, toes or other parts of the body, comprising a piece of fabric assembled so as to form a sleeve, and at least one lining layer fixed onto a face of the piece of fabric.

This patent more particularly describes, with reference to its FIGS. 1 to 5, a protective sleeve comprising two pieces of fabric assembled by welding or stitching along their edges to form the body of the sleeve. The lining layer is first fixed onto a face of one of the two pieces of fabric, and the sleeve is turned inside out before being used, so that the lining film is inside the sleeve.

Patent EP 1 191 912 B also describes, with reference to its FIGS. 6 to 8, an embodiment of the protective sleeve using only one piece of fabric that first receives the lining layer and that is then folded and assembled by making two weld or stitch assembly seams, which are perpendicular to the fold line of the piece of fabric. A sleeve closed at one of its ends is thus obtained, the closed end corresponding to the fold line.

This method for producing a sleeve using only one piece of fabric is advantageous as it simplifies the manufacturing process. However, it does not enable a sleeve to be obtained that has its two ends open, or a plurality of sleeves to be produced collectively.

Moreover, in the first or second embodiment described by EP 1 191 912 B, despite the sleeve being turned inside out, the weld or stitch assembly seams form excessive thicknesses or assembly overlaps, or even zones of hardened material that can irritate the skin. In certain persons, such as diabetic people suffering from neuropathies or arteriopathies, such irritations eventually cause the formation of lesions.

BRIEF SUMMARY OF THE INVENTION

Thus, one object of the present invention is to produce a sleeve for the protection or care of fingers or toes that has optimal features in terms of protection and comfort.

Another object of the present invention is to provide a method for manufacturing a protective sleeve that is simple to implement and having a low cost price.

Yet another object of the present invention is to provide a method for manufacturing a protective sleeve that enables a protective sleeve to be produced from a single piece of fabric.

Yet another object of the present invention is to provide a method for manufacturing a protective sleeve that enables a plurality of protective sleeves to be produced collectively.

To achieve these objects, one principle of the present invention is to form a sleeve by folding a piece of fabric and by making a single assembly seam parallel to the fold line of the fabric. Another principle of the present invention is to arrange the lining layer of the sleeve after having performed the steps of folding and assembling the piece of fabric, and of arranging this lining layer on the assembly seam, so that an assembly overlap is covered in whole or in part by the lining layer.

More particularly, the present invention provides a sleeve for protecting a part of the body, comprising a piece of fabric assembled so as to form a sleeve, and at least one lining layer fixed onto a face of the piece of fabric. According to the present invention, the piece of fabric has only one assembly seam linking two of its edges and extending in parallel to a fold line of the piece of fabric, and the lining layer at least partially covers the assembly seam.

According to one embodiment of the present invention, the lining layer is made of a viscoelastic gel.

Advantageously, the viscoelastic gel is self-adhesive.

According to one embodiment of the present invention, the piece of fabric comprises elastic fibers.

According to one embodiment of the present invention, the piece of fabric comprises thermoplastic fibers and the assembly seam is a weld seam.

According to one embodiment of the present invention, the assembly seam is a stitch seam.

According to one embodiment of the present invention, the piece of fabric comprises a combination of polyamide fibers and elastane fibers.

According to one embodiment of the present invention, the lining layer is fixed by being adhered to the piece of fabric.

The present invention also relates to a method for manufacturing at least one sleeve for protecting a part of the body, the sleeve comprising a piece of fabric assembled so as to form a sleeve, and at least one lining layer fixed onto a face of the piece of fabric. According to the present invention, the method comprises steps of:

folding the piece of fabric and assembling two opposite edges of the piece of fabric along an assembly seam parallel to a fold line of the piece of fabric, to form a tube having two open ends, and fixing at least one lining layer onto an external face of the piece of fabric, at least partially covering the assembly seam.

According to one embodiment of the present invention, the piece of fabric comprises thermoplastic fibers, and the assembly seam is produced by welding the opposite edges of the piece of fabric.

According to one embodiment of the present invention, the assembly line is produced by stitching the opposite edges of the piece of fabric.

According to one embodiment of the present invention, the method comprises a step of cross cutting the tube when flat to obtain a plurality of sleeves.

According to one embodiment of the present invention, the method comprises a step of turning the sleeve inside out to arrange the lining strip on the internal face of the sleeve.

According to one embodiment of the present invention, the method comprises a step of cutting an excess of fabric between the assembly seam and the ends of the opposite edges of the piece of fabric.

According to one embodiment of the present invention, the lining layer is fixed by being adhered to the piece of fabric.

According to one embodiment of the present invention, the method comprises steps of:

folding the piece of fabric over in the form of a strip along a fold line, so as to arrange longitudinal edges of the strip against each other, assembling the longitudinal edges of the strip along an assembly seam, so as to obtain a flat tube of fabric, turning the tube of fabric about itself, so as to present the assembly seam substantially in the middle of a visible face of the flat tube, winding the tube, so as to form a roll, providing a lining strip made of a viscoelastic gel laid down flat on a medium, and unwinding the roll onto the lining strip while adhering the lining strip to the tube, so as to cover the assembly seam.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
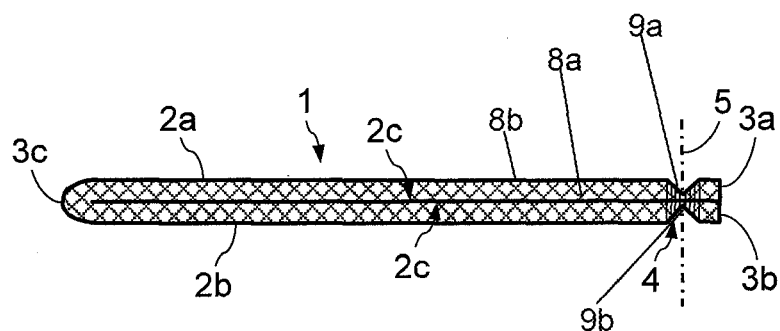
FIGS. 1 to 4 are schematic, transverse cross-sections represented in a flat condition, showing steps of a method for manufacturing a protective sleeve according to an embodiment of the present invention.

During a step shown in FIG. 1, a strip of rectangular fabric is folded over itself longitudinally, along a median fold line 3c. The strip of fabric has a first main face 8a and an opposing second main face 8b (see, e.g., FIG. 1). The first main face 8a includes a first edge region 9a extending proximate to and along the first edge 3a and a second edge region 9b extending proximate to and along the second edge 3b (see, e.g., FIG. 1). The first longitudinal edge 3a and the second opposing longitudinal edge 3b of the strip of fabric, and more particularly the first and second edge regions 9a, 9b of the first main face 8a, thus placed against each other, are assembled one against the other by making a weld seam 4 parallel to the fold line 3c, contrary to the method described in patent EP 1 191 912 B (FIGS. 6 to 8), which provides for two weld seams made perpendicular to the fold line. As such, the weld seam 4 extends within the assembled first and second edge regions 9a, 9b (see, e.g., FIG. 1).

A tube 1 is thus obtained, whose ends are open, instead of a sleeve having a closed end, and having only one assembly seam, here a weld seam.

In FIG. 1 and during steps described below and shown in FIGS. 2 to 4, the tube 1 is arranged flat on a work surface (not represented) and has a substantially flattened shape, that is represented schematically in these Figures as being perfectly flattened. The tube thus has an upper external face 2a, a lower external face 2b, and two internal faces 2c which are opposite each other.

The weld seam 4 is produced classically using an ultrasonic welding or heat sealing machine, producing a local temperature rise generating a fusion of the fabric. For this purpose, the strip of fabric comprises thermoplastic fibers. The fabric also preferably comprises elastic fibers, giving the tube the desired elasticity.

Figure 2:
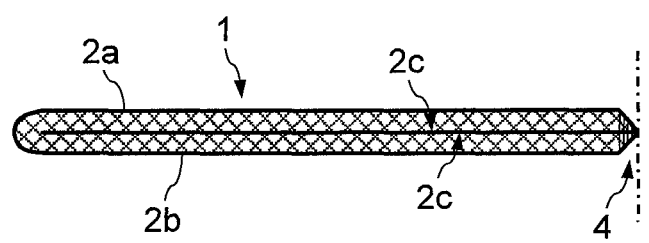

During the step shown in FIG. 2, the excess fabric at the assembled edges is removed by cutting along a cutting line 5, and more particularly along the single assembly seam. Preferably, the edges of the fabric are cut at the time of the welding by the welding tool, which melts the fabric down. That is, the welding cuts the excess of fabric extending between the first and second opposing edges of the single piece of fabric and the single assembly seam. The welding zone then forms, in cross-section, a sort of peak of hardened material.

Figure 3:
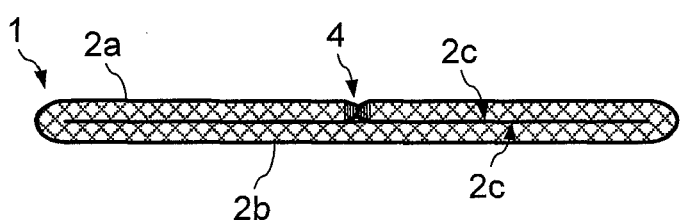

During the step shown in FIG. 3, the tube 1 is turned about itself so as to take the weld seam 4 to the upper external face 2a of the tube 1, that is still arranged flat. The weld seam is preferably placed substantially in the middle of the upper external face 2a. During the movement of rotating the tube about itself, the assembled edges 3a, 3b move away to form an edge-to-edge link of the fabric. Thus, the assembly of the edges of the strip of fabric does not form any excessive thickness capable of causing the user discomfort or lesions.

Figure 4:
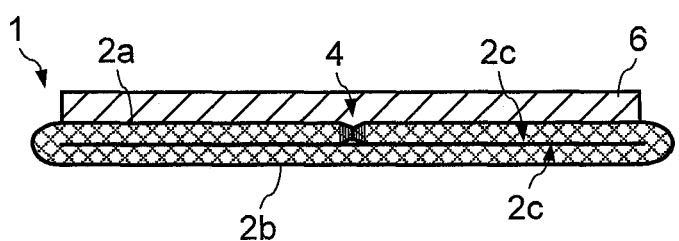

During a next step, shown in FIG. 4, a lining 6 is fixed onto the tube 1, so as to cover the weld seam 4, at least partially and preferably in its entirety. Advantageously, the lining 6 is a strip made up of a viscoelastic silicone gel having a uniform thickness from a few tenths of a millimeter to a few millimeters, and preferably on the order of 1 mm. The lining 6 is manufactured, for example, at the desired thickness and cut into strips having the same width as the flat tube 1, for example by means of rotating cutters.

The lining is assembled on the tube 1 by being adhered to the upper external face 2a of the tube. For example, the flat tube 1 of fabric is unwound and put in contact with a strip of silicone gel having substantially the same width, by disposing glue or other adhesive between the upper external face 2a and the strip of gel. In one alternative embodiment the strip of silicone gel and/or the upper external face of the tube are pre-pasted.

Before the fixation of the strip of silicone gel, the tube 1 can be wound so as to form a roll, while the strip of silicone gel is laid down flat on a medium. The tube is then unwound over the strip of silicone gel by previously pasting one and/or the other of the faces opposite the tube and the strip of silicone gel. The tube 1 can thus be manufactured almost continuously, which reduces offcuts of fabric.

The tube 1 according to the embodiment of the present invention provided here, having a length clearly greater than the usual length of a protective sleeve, is then cut up so as to obtain sleeves having a desired length.

Figure 5:
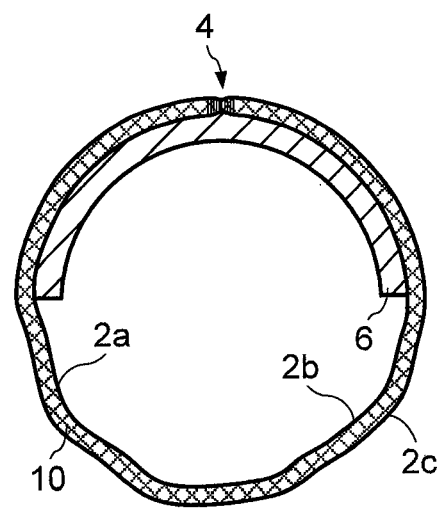
FIG. 5 is a schematic, transverse cross-section of the sleeve manufactured according to the method illustrated in FIGS. 1 to 4, ready to be used for protection of a finger or a toe.

As shown in FIG. 5, the cut sleeves 10 obtained by cutting the tube 1 are turned inside out at the time of use, so that the lining 6 is inside the sleeve. However, such turning is optional given that the sleeve according to the present invention can also be used with the layer of viscoelastic gel disposed outside, for example to protect a finger adjacent to the one covered by the sleeve.

The sleeve 10 thus obtained has no visible assembly seam on the side onto which the lining 6 is fixed. The lining 6, adhered to the tube of fabric on either side of the weld seam 4 and on the weld seam itself, strengthens the weld seam and thus limits the risk of tearing.

In addition, when the mode for assembling the edges of the fabric causes the formation of an overlap, the overlap is advantageously covered by a layer of viscoelastic gel that loses its shape when it is fixed, so as not to form any excessive thickness on its face intended to come into contact with the skin.

The strip of fabric constituting the tube 1 of fabric preferably comprises a combination of elastic fibers comprising elastane and of thermoplastic fibers comprising polyamide. As an example, the strip of fabric comprises 70% of polyamide fibers and 30% of elastane fibers. Advantageously, the basis weight of the strip of fabric is less than 250 g/cm$^2$. Preferably, the fabric chosen is run-resistant to avoid any fraying as a result of the tube being cut into sleeves.

The silicone gel forming the lining 6 preferably has properties of viscoelasticity similar to the mechanical properties of certain human skin tissues. Compositions with mixtures of silicone gels having such properties have been described in French Patent FR 2 712 487, which is referred to for details of formulation and elaboration. These compositions have the particular feature of reproducing the mechanical properties of the natural footpad and particularly of having similar values of compression and torsion moduli. Silicone gels having such formulations are marketed by the Millet Innovation under the trademark EPITHELIUM 26®. Other formulations, marketed by the Millet Innovation under the trademarks EPITHELIUM 27® and EPIHELIUM 27+®, also enable, sometimes to the detriment of the similarity of the mechanical compression and torsion moduli, intrinsic adhesion properties of the silicone gel to be obtained. These gels have exceptional contact qualities and constitute excellent load spreaders, capable of producing remarkable results in terms of comfort and prevention, as well as treating certain conditions, in particular hyperkeratoses. In practice, the conformity of these gels can be verified by checking the compression and torsion moduli, whose nominal values are on the order of 4.10$^3$ N/m$^2$ and from 4.10$^3$ N/m to 15.10$^3$ N/m$^2$, respectively. A 50% tolerance compared to the limit values of these moduli can be accepted without losing the advantages of these gels for the medical or paramedical application targeted here.

Thus, according to one preferred embodiment of the present invention, the gel forming the lining 6 of the tube 1 is a silicone viscoelastic gel, whose mechanical properties are on the order of those of the human footpad, the gel particularly having compression and torsion moduli on the order of half to twice the corresponding moduli of the footpad. This gel is, for example, the abovementioned silicone gel marketed under the trademark EPITHELIUM 26®.

In an alternative embodiment, in addition to mechanical properties similar to the human footpad, the silicone gel has the property of being intrinsically adhesive by the effect of mere contact with the skin, and the gel can be unstuck and stuck again nearly indefinitely. This gel is, for example, the silicone gel marketed under the trademarks EPITHELIUM 27® or EPITHELIUM 27+®.

Figure 6:
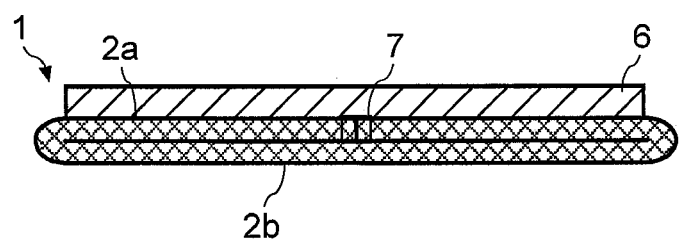
FIG. 6 is a schematic, transverse cross-section, represented in a flat condition, of an alternative embodiment of a protective sleeve according to the present invention.

In an alternative embodiment of the sleeve according to the present invention, shown in FIG. 6, the two edges 3a, 3b of the strip of fabric are assembled edge to edge by a flat seam 7 that does not form any excessive thickness. As the seam, for example formed by stitching, is covered by the strip of silicone gel 6, there is no risk of irritating the skin.

It will be understood by those skilled in the art that various other alternative embodiments and applications of the device according to the present invention are possible. Thus, the present invention is not limited to the collective manufacturing of sleeves using a strip of fabric. Such a sleeve can also be obtained using a rectangular piece of fabric. It is not essential either to cut the excess edges off the piece of fabric once fixed. Indeed, the weld can be done right up to the edges 3a, 3b. Using an elastic fabric is not necessary either. This feature is merely preferable for the sake of ease of use of the sleeve.

Moreover, although it is indicated in the present application that the sleeve according to the present invention has only one assembly seam, by contrast with the method described in Patent EP 1 191 912 B, it goes without saying that this assembly seam, particularly if it is produced by stitching, may comprise several parallel seams close together, forming a single assembly seam within the meaning of the present invention.

Similarly, other fixation means can be considered to fix the layer of viscoelastic gel.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for manufacturing at least one sleeve for protecting a part of a body, the at least one sleeve comprising only a single assembly seam which ensures that the at least one sleeve may be worn on the part of the body without breaking, the method comprising:

providing a single piece of fabric having a first edge and an opposing second edge, and a first main face and an opposing second main face, the first main face including a first edge region extending proximate to and along the first edge and a second edge region extending proximate to and along the second edge;

folding the single piece of fabric along a median folding line to arrange the first and second edge regions of the first main face against each other;

forming the single assembly seam so as to assemble together the first and second edge regions to obtain a flat tube having two open ends and the single assembly seam, the single assembly seam extending within the assembled first and second edge regions;

removing, by cutting along the single assembly seam, excess fabric extending between the first and second opposing edges and the single assembly seam;

presenting the single assembly seam in an upper external face of the flat tube; and fixing at least one lining strip made of viscoelastic gel onto the upper external face of the flat tube, such that the viscoelastic gel is directly in contact with and at least partially covers the single assembly seam and the assembled first and second edge regions.

2. The method according to claim 1, wherein the single piece of fabric is a single strip of fabric and the step of fixing the at least one lining strip onto the upper external face of the flat tube comprises the steps of:

winding the flat tube to form a roll;

laying the at least one lining strip flat on a medium, the at least one lining strip comprising a viscoelastic gel; and unwinding the roll onto the at least one lining strip, such that the at least one lining strip is fixed onto the single assembly seam and the first and second edge regions of the first main face of the single strip of fabric which are assembled together.

3. The method according to claim 2, wherein the single strip of fabric comprises thermoplastic fibers and the single assembly seam is produced by welding the first and second opposing edges of the single strip of fabric, which welding cuts the excess of fabric extending between the first and second opposing edges of the single strip of fabric and the single assembly seam.

4. The method according to claim 2, comprising a step of cross cutting the flat tube of fabric to obtain a plurality of sleeves.

5. The method according to claim 2, comprising a step of turning the at least one sleeve inside out to arrange the at least one lining strip on an internal face of the sleeve.

6. The method according to claim 1, wherein the single piece of fabric comprises thermoplastic fibers and the single assembly seam is produced by welding the first and second opposing edge regions of the first main face of the single piece of fabric, which welding cuts the excess of fabric extending between the first and second opposing edges of the single piece of fabric and the single assembly seam.

7. The method according to claim 1, wherein the single assembly seam is produced by stitching the first and second opposing edge regions of the first main face of the single piece of fabric.

8. The method according to claim 1, comprising a step of cross cutting the flat tube to obtain a plurality of sleeves.

9. The method according to claim 1, comprising a step of turning the at least one sleeve inside out to arrange the at least one lining strip on an internal face of the sleeve.

10. The method according to claim 1, wherein the at least one lining strip is fixed by adhering to the single piece of fabric.

11. The method according to claim 1, wherein the step of presenting the single assembly seam in an upper external face of the flat tube comprises rotating the flat tube of fabric about a longitudinal axis thereof until the single assembly seam is presented in the upper external face of the flat tube.

* * * * *